US00PP15555P2

(12) United States Plant Patent
Tristram

(10) Patent No.: US PP15,555 P2
(45) Date of Patent: Feb. 15, 2005

(54) ***GAURA* PLANT NAMED 'WALGAUPF'**

(50) Latin Name: *Gaura lindheimeri*
Varietal Denomination: Walgaupf

(76) Inventor: David Tristram, Walberton Nursery, Yapton Lane, Walberton, Arundel (GB), BN18 OAS ( * ) Notice: Subject to any disclaimer, the term of this patent is extended or adjusted under 35 U.S.C. 154(b) by 171 days.

(21) Appl. No.: 10/456,154

(22) Filed: Jun. 6, 2003

(51) Int. Cl.[7] ..... A01H 5/00
(52) U.S. Cl. ..... Plt./226
(58) Field of Search ..... Plt./226

*Primary Examiner*—Anne Marie Grunberg
*Assistant Examiner*—S B McCormick-Ewoldt

(57) ABSTRACT

A new cultivar of *Gaura* plant named 'Walgaupf' a perennial plant characterized by red young foliage and green mature foliage, pink flowers, dense floriferous blooming and upright habit. In combination these traits set 'Walgaupf' apart from all other existing varieties of *Gaura* known to the inventor.

1 Drawing Sheet

Genus: *Gaura*.
Species: *lindheimeri*.
Denomination: Walgaupf.

BACKGROUND OF THE INVENTION

The present invention relates to a new and distinct variety of butterfly bush grown as an ornamental for its profuse display of pink flowers. The new cultivar is known botanically as *Gaura lindheimeri* and will be referred to hereinafter by the cultivar name 'Walgaupf'.

'Walgaupf' is a seedling selection that was selected by the inventor in the summer of 2000 out of two-hundred seedlings that resulted from the induced cross between *Gaura* 'White Fountain' (unpatented) and *Gaura* 'Siskyou Pink' (unpatented). The female parent plate is *Gaura* 'White Fountain' and the male parent plant is *Gaura* 'Siskyou Pink'. The selection was conducted in a cultivated area of Sussex, United Kingdom and resulted from a formal breeding program designed to produce new and improved varieties of *Gaura*. Seedling selection was based on number of open flowers per flower spike.

The female parent, *Gaura* 'White Fountain', has pure white flowers and a dense upright habit. 'Walgaupf' exhibits similar dense habit characteristics but has pink flowers as further described herein.

The closest comparison plant to 'Walgaupf' is *Gaura* 'Siskyou Pink'. The Flower spikes of Siskiyou Pink exhibits 2–3 flowers open at a time per spike when in full growth. In contrast 'Walgaupf' exhibits an average of 5–8 flowers open at a time per flower spike when in full growth. This confers a dense flowering effect as opposed to the customary wispy flowering effect.

'Walgaupf' was first asexually propagated in 2000 by the inventor in a cultivated area of Sussex, United Kingdom. The original seedling was selected out, planted in the breeders test garden and propagated by stem cuttings. Subsequent stock is derived from this single plant. Since that time the characteristics of the new cultivar have been determined stable and are reproduced true to type in successive generations.

SUMMARY OF THE INVENTION

The following traits have been repeatedly observed and represent the distinguishing characteristics of the new plant 'Walgaupf'. In combination these traits set 'Walgaupf' apart from all other *Gaura* known to the inventor. 'Walgaupf' has not been tested under all possible conditions and phenotypic differences may be observed with variations in environmental, climatic and cultural conditions, however, without any variance in genotype.

1. *Gaura* 'Walgaupf' exhibits a dense upright habit.
2. *Gaura* 'Walgaupf' is propagated using stem cuttings.
3. *Gaura* 'Walgaupf' produces a floriferous display of pink flowers with 5–8 open flowers at a time per spike when in full growth.
4. *Gaura* 'Walgaupf' is hardy in USDA Zones 5–10.
5. *Gaura* 'Walgaupf' is 45–64 cm. in height and 50–65 cm. in width in a 1-liter container.
6. *Gaura* 'Walgaupf' exhibits red young foliage and green mature foliage.

BRIEF DESCRIPTION OF THE DRAWING

The accompanying color drawing illustrates the overall appearance of the new cultivar 'Walgaupf' showing the colors as true as it is reasonably possible to obtain in colored reproduction of this type. Colors in the drawing may differ from the color values cited in the detailed botanical description which more accurately describe the actual colors of the new variety 'Walgaupf'. The plant in the drawing was grown in Arroyo Grande, Calif. in a one-liter container. The plant was 12-months-old at the time and grown out-of-doors.

The drawing on sheet 1 illustrates an entire plant in bloom from a side perspective. The photograph was made using conventional techniques and although colors may appear different from actual colors due to light reflectance they are as accurate as possible by conventional photography.

BOTANICAL DESCRIPTION OF THE PLANT

The following is a detailed description of the new *Gaura* plant named 'Walgaupf'. Data was collected in Arroya Grande Calif. from 12-month-old plants grown in one-liter containers and grown out-of-doors. The color determinations are in accordance with the 2001 Royal Horticultural Society Colour Chart of The Royal Horticultural Society, London, England, except where general color terms of ordinary dictionary significance are used. The growing requirements are similar to other *Gaura*.

Botanical classification: *Gaura* 'Walgaupf'.
Species: *lindheimeri*.
Commercial classification: Perennial.
Common name: Butterfly bush.
Use: Ornamental for container or landscape.
Cultural requirements: Plant in well-drained moderately fertile soil in full sun.
Root system: Deep rooting makes the plant very drought tolerant.
Parentage: *Gaura* 'Walgaupf' is a seedling selection that resulted from the induced hybridization between the following parent plants:
*Female parent plant.*—*Gaura* 'White Fountain'.
*Male parent plant.*—*Gaura.* 'Siskyou Pink'.
Plant description:
*Bloom period.*—Late spring to fall.
*Plant habit.*—Upright, dense perennial.
*Height.*—45–64 cm. in height from soil level in a 1-liter container.
*Width.*—50–65 cm. in width in a 1-liter container.
*Hardiness.*—USDA Zones 5–10.
*Propagation.*—Propagation is accomplished using stem cuttings.
*Time to develop roots.*—2–3 weeks are needed for initial cuttings to develop roots.
*Crop time.*—4–6 months are needed to produce a finished 1-liter container.
*Disease Resistance/Susceptibility.*—In common with other varieties of *Gaura* known to the inventor, 'Walgaupf' is considered disease-free under ordinary greenhouse and garden growing conditions.
Stem:
*Shape.*—Round to slightly oval in cross-section.
*Stem color.*—The base of the stem and young growth are 185A and the remaining surface of the stem is 138A. Both colors are present on the stem.
*Stem dimensions.*—22 cm. in length and 2.5 mm. in diameter.
*Stem surface.*—Pubescent.
*Color of pubescence.*—156D.
*Internode length.*—1–2 cm. between nodes.
*Branching habit.*—Open, branching from both base and stems.
Foliage:
*Shape.*—Closest to oblanceolate.
*Division.*—Simple.
*Apex.*—Acuminate.
*Base.*—Attenuate.
*Venation* (*abaxial surface*).—One prominent mid-vein protruding.
*Vein color* (*adaxial surfaces*).—185C.
*Vein color* (*abaxial surfaces*).—185C.
*Margins.*—Entire or slightly serrate.
*Quantity of leaves per stem.*—Average of 15 leaves per stem.
*Arrangement.*—Spiral and alternate.
*Attachment.*—Sessile.
*Leaf surface* (*adaxial and abaxial surfaces*).—Pubescent.
*Leaf dimensions.*—3–8 cm. in length and 1–1.5 cm. in width.
*Leaf color* (*adaxial surface*).—Mature leaves 137B, young leaves 59A.
*Leaf color* (*abaxial surface*).—Mature leaves 138A, young leaves 176B.
Flowers:
*Inflorescence.*—Spike.
*Dimensions of inflorescence.*—21 cm. in length and 4 cm. in width.
*Quantity of combined flowers and buds per inflorescence.*—17 to 25 combined buds and flowers per inflorescence.
*Shape.*—Explanate.
*Sexuality.*—Bisexual.
*Flower dimensions.*—3 cm. in diameter and 3 cm. in length.
*Persistent or self-cleaning.*—Self-cleaning.
*Aspect.*—Facing outward.
*Bud dimensions.*—3 mm. in width and 1.50 cm. in length.
*Bud shape.*—Linear.
*Bud color.*—185B.
*Bud surface.*—Pubescent.
*Flower color.*—64C with darker veins that are 64A in color.
*Calcar.*—Two in number.
*Calcar surface.*—Pubescent.
*Dimensions of calcar.*—1.50 cm. in length and 2 mm. in diameter.
*Color of calcar.*—64B.
*Petals.*—Four in number.
*Petal shape.*—Closest to ovate.
*Petal dimensions.*—2 cm. in length and 1 cm. in width.
*Fused or unfused.*—Unfused.
*Petal margin.*—Entire.
*Petal surface.*—Glabrous.
*Peduncle dimensions.*—2–9 mm. in length and 1–2 mm. in diameter.
*Peduncle color.*—64A.
*Peduncle surface.*—Pubescent.
*Pedicel.*—Very short or absent.
*Fragrance.*—No fragrance.
Reproductive organs:
*Stamens.*—Eight.
*Stamen color.*—69D.
*Stamen dimensions.*—6 mm. in length and 0.5 mm. in diameter.
*Anther color.*—61A.
*Anther dimensions.*—3 mm. in length and 0.50 mm. in width.
*Quantity of pollen.*—Small amount.
*Color of pollen.*—161A.
*Pistil.*—One.
*Pistil dimensions.*—12 mm. in length and 0.50 mm. in width.
*Pistil color.*—158A.
*Pistil shape.*—Filament.
*Style color.*—61A.
*Stigma shape.*—Four lobed.
*Stigma color.*—161A.
*Ovary position.*—Inferior. sessile.
*Ovary color.*—176B.
*Ovary shape.*—Linear.
*Ovary dimensions.*—6 mm. in height and 2 mm. in diameter.
Seed production: No seed production has been observed to date.

I claim:

1. A new and distinct cultivar of *Gaura* plant named 'Walfaupf' as described and illustrated.

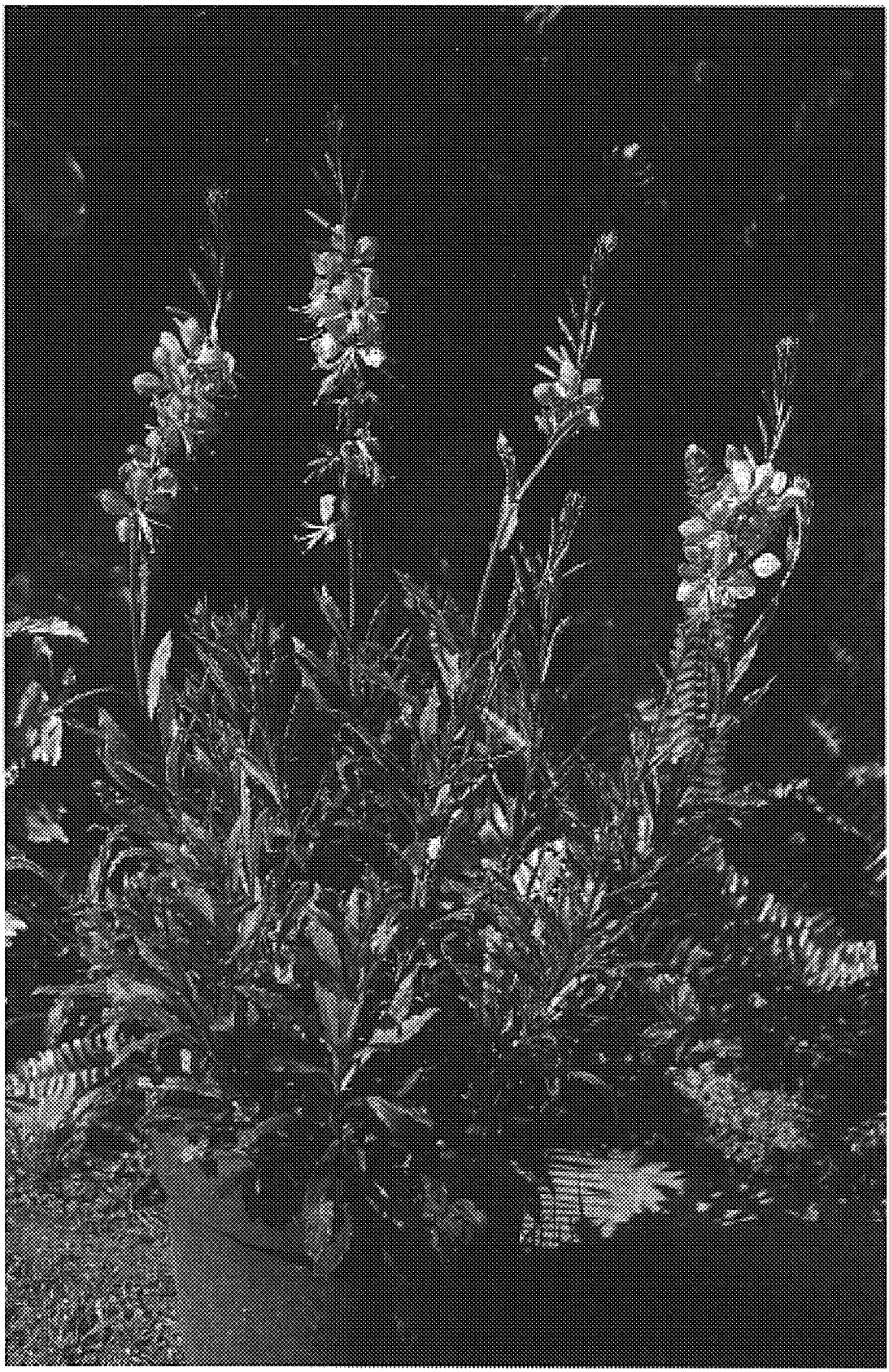

* * * * *